「United States Patent」[19]

DeLuca et al.

[11] Patent Number: 4,552,698
[45] Date of Patent: * Nov. 12, 1985

[54] 23,23-DIFLUORO-1α,25-DIHYDROXY-VITAMIN $D_3$

[75] Inventors: Hector F. DeLuca; Yoko Tanaka, both of Madison, Wis.; Nobuo Ikekawa; Yoshiro Kobayashi, both of Tokyo, Japan

[73] Assignee: Wisconsin Alumni Research Foundation, Madison, Wis.

[*] Notice: The portion of the term of this patent subsequent to Mar. 5, 2002 has been disclaimed.

[21] Appl. No.: 639,778

[22] Filed: Aug. 13, 1984

Related U.S. Application Data

[63] Continuation-in-part of Ser. No. 524,268, Aug. 18, 1984, Pat. No. 4,502,991.

[51] Int. Cl.$^4$ ............................................. C07J 9/00
[52] U.S. Cl. .............................. 260/397.2; 260/397.1; 260/239.5
[58] Field of Search ..................................... 260/397.2

[56] References Cited

U.S. PATENT DOCUMENTS 4,284,577  8/1981  Yamada et al. .................. 260/397.2

Primary Examiner—Elbert L. Roberts
Attorney, Agent, or Firm—Howard W. Bremer

[57] ABSTRACT

The invention provides new derivatives of vitamin D, 23,23-difluoro-1,25-dihydroxycholecalciferol and the acylates thereof.

The derivative compounds are characterized by vitamin D-like activity.

4 Claims, No Drawings

23,23-DIFLUORO-1α,25-DIHYDROXY-VITAMIN D3

The invention described herein was made in the course of work under a grant or award from the Department of Health and Human services.

The Government also has rights in this invention pursuant to U.S. Japan Cooperative Grant INT-76-05793 awarded by the National Science Foundation.

This application is a continuation-in-part of application Ser. No. 524,268, filed Aug. 18, 1984 now U.S. Pat. No. 4,502,991.

TECHNICAL FIELD

This invention relates to a compound which is characterized by vitamin D-like activity.

More specifically this invention relates to a derivative of vitamin $D_3$.

Vitamin $D_3$ is a well-known agent for the control of calcium and phosphorous homeostasis. In the normal animal or human this compound is known to stimulate intestinal calcium transport and bone-calcium mobilization and is effective in preventing rickets.

It is also now well known that to be effective, vitamin $D_3$ must be converted in vivo to its hydroxylated forms. For example, the vitamin is first hydroxylated in the liver to form 25-hydroxy-vitamin $D_3$ and is further hydroxylated in the kidney to produce 1α,25-dihydroxy-vitamin $D_3$ or 24,25-dihydroxy-vitamin $D_3$. The 1-hydroxylated form of the vitamin is generally considered to be the physiologically active or hormonal form of the vitamin and to be responsible for what are termed the vitamin D-like activities, such as increasing intestinal absorption of calcium and phosphate, mobilizing bone mineral, and causing reabsorption of calcium in the kidneys.

BACKGROUND ART

Since the discovery of biologically active metabolites of vitamim D there has been much interest in the preparation of structural analogs of these metabolites, because such compounds may represent useful therapeutic agents for the treatment of diseases resulting from calcium metabolism disorders. A variety of vitamin D-like compounds have been synthesized. See, for example, U.S. Pat. Nos. 3,741,996 directed to 1α-hydroxycholecalciferol; 3,907,843 directed to 1α-hydroxyergocalciferol; 3,786,062 directed to 22-dehydro-25-hydroxycholecalciferol; 4,069,321 directed to the preparation of various side chain-fluorinated dihydrotachysterol analogs; 4,201,881 directed to 24,24-difluoro-1α,25-dihydroxycholecalciferol and 4,196,133 directed to 24,24-difluoro-25-hydroxycholecalciferol. Other metabolic alternatives are believed to be responsible for the metabolism and ultimate elimination of vitamin D compounds from the body, with the generally accepted recognition that 1α,25-dihydroxycholecalciferol (U.S. Pat. No. 3,697,559) is the circulating hormonal form of vitamin D.

DISCLOSURE OF INVENTION

A new derivative of vitamin D has now been found which is at least as potent as 25-hydroxyvitamin $D_3$ (see U.S. Pat. No. 3,565,924) as measured by its ability to stimulate calcium transport in the intestine or its ability to mobilize calcium from bone. This derivative has been identified as 23,23-difluoro-1α,25-dihydroxycholecalciferol (23,23-difluoro-1,25-dihydroxy vitamin $D_3$ or 23,23-$F_2$-1,25(OH)$_2$$D_3$).

A major pathway for inactivation of vitamin is 23S-hydroxylation of 25-hydroxy vitamin $D_3$ (Tanaka et al, Biochemistry 20, 3875–3879, 1981) and its subsequent conversion to 25R-hydroxy-26,23S-lactone (Tanaka et al, Proc. Nat'l. Acad. Sci. USA 78, 4805–4808, 1981). In view of these findings of Tanaka et al it would appear that the vitamin D derivative of the present invention, because of the fluorine substituents at C-23 would not be readily hydroxylated at that carbon and that, therefore, it would be characterized by prolonged vitamin D-like activity—a characteristic which would be an obvious advantage in many therapeutic applications.

BEST MODE FOR CARRYING OUT THE INVENTION 23,23-Difluoro-1α,25-dihydroxy-vitamin $D_3$ can be readily prepared from 23,23-difluoro-25-hydroxy-vitamin $D_3$ by in vitro enzymatic hydroxylation of the latter compound at carbon 1 as illustrated in the following scheme:

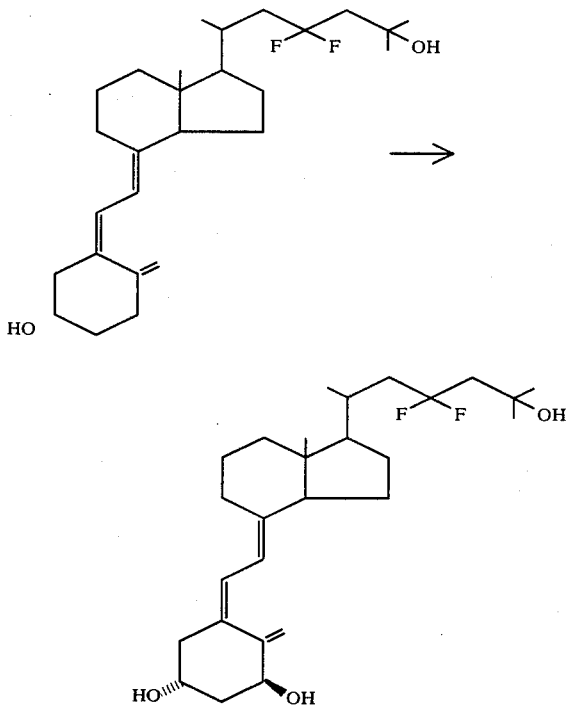

Hydroxylation at carbon 1 can be accomplished by incubating the precursor 23,23-difluoro-25-hydroxy-vitamin $D_3$ with a homogenate prepared from kidney tissue of vitamin D-deficient chickens.

One day-old leghorn chickens were fed a vitamin D-deficient diet containing 1% calcium for two weeks (Omdahl et al, Biochemistry, 10, 2935–2940 (1971). They were then killed, their kidneys were removed, and a 20% (W/V) homogenate was prepared in ice-cold 0.19M sucrose solution containing 15 mM. Tris-acetate(trihydroxymethylaminoethane acetate) (pH 7.4 at room temperature) and 1.9 mM magnesium acetate (Tanaka, Y. et al, Arch. Biochem. Biophys. 171, 521–526 (1975). The incubation involved the addition of 9 µg of 23,23-difluoro-25-hydroxyvitamin $D_3$ dissolved in 100 μl of 95% ethanol to a 125 ml Erlenmeyer flask which contained 1 g of kidney tissue, 0.19M sucrose, 1.5 mM Trisacetate, 1.9 mM magnesium acetate and 25 mM succinate in the final volume of 7.5 ml. After shaking the mixture at 37° C. for 2 hrs., the reaction was stopped with 15 ml of MeOH and 7.5 ml of $CH_2Cl_2$. After another 7.5 ml of $CH_2Cl_2$ was added the organic phase, the resulting mixture was separated and evaporated under vacuum. The residue containing the desired 23,23-difluoro-1,25-dihydroxyvitamin $D_3$ was then subjected to chromatographic purification by high pressure liquid chromatography using a model ALC/GPC 204 high pressure liquid chromatograph (Waters Associates, Medford, Mass.) equipped with an ultraviolet detector operating at 254 nm. The residue, dissolved in 100 μl of 10% 2-propanol in hexane, was injected onto a silica gel column (Zorbax-SIL, 0.46×25 cm, Dupont, Inc.) operating under a pressure of 1000 psi which produced a flow rate of 2 ml/min. Using a solvent system containing 10% 2-propanol in hexane, the sample was purified twice through this column and then collected. Putative 23,23-difluoro-1,25-dihydroxyvitamin $D_3$ was further purified on a reverse-phase column (Lichrosorb RP-15, 0.46×25 cm, E. Merck, Darmastadt, Federal Republic of Germany) using the same high pressure liquid chromatograph operating at a pressure of 2000 psi. The product was eluted with a solvent mixture of $H_2O$/MeOH (1/4) and collected. The residue was rechromatographed on the Zorbax SIL column using conditions exactly as described above.

The identity of the product as 23,23-difluoro-1,25-dihydroxy vitamin $D_3$ was confirmed by its spectroscopic properties. The compound showed the typical vitamin D-like ultraviolet absorption with a maximum at 264 nm. The mass spectrum of the product contained a molecular ion at m/e 452 as required for a 23,23-difluoro-1,25-dihydroxyvitamin $D_3$. Fragments at m/e 434 and 416 represent elimination of one and two molecules of $H_2O$. Loss of the entire side chain results in the fragment of m/e 287 which, by elimination of one and two molecules of $H_2O$, gives rise to peaks at m/e 269 and 251. In addition, the spectrum shows prominent peaks at m/e 152 and m/e 134 (elimination of one molecule of $H_2O$) which represent ring A fragments and are diagnostic for $1\alpha,3\beta$-dihydroxyvitamin $D_3$ compounds.

The compound of this invention, 23,23-difluoro-$1\alpha$,25-dihydroxyvitamin $D_3$, can be obtained in crystalline form if desired by recrystallization from appropriate hydrocarbon solvents, or combinations of such solvents with alcoholic solvents, e.g. a combination of hexane and methanol, as is well known in the organic chemical arts.

If desired the free vitamin of this invention can be readily converted to its acylated form with the compounds of this invention then being broadly represented by the formula

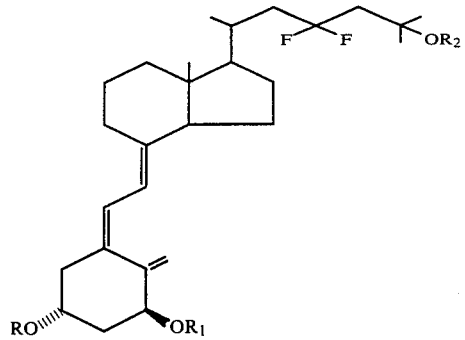

where R, $R_1$ and $R_2$ are each selected from the group consisting of hydrogen, an acyl group having from one to about four carbon atoms and benzoyl. The conversion from the free vitamin to the acylate can be readily accomplished by reacting the free vitamin with the appropriate acyl chloride or anhydride, the acyl group of which will correspond to the acyl group which is desired to be present at either of the one, three or twenty-five position in the molecule, in pyridine at a temperature in the range from ambient temperature to reflux. For example, treatment of the free vitamin (1 mg) with acetic anhydride (0.1 ml) in pyridine (0.1 ml) at ambient temperature for 1.5 hours yields the corresponding 1,3-diacetoxy derivative. The corresponding 1,3,25-triacetoxy derivative can be readily obtained by utilizing the same reagents at elevated temperatures, e.g. 75°–90° C. Similarly, the corresponding benzoate compound can be prepared by reaction of the free vitamin with benzoyl chloride in pyridine at room temperature for three hours.

Other acylates can also be prepared under like conditions with like reagents as will be readily evident to those skilled in the art.

SYNTHESIS OF STARTING MATERIAL

The 23,23-difluoro-25-hydroxyvitamin D from which 23,23-difluoro-$1\alpha$,25-dihydroxyvitamin $D_3$ is derived by the foregoing process can be obtained in accordance with the process hereinafter described and shown in the accompanying schematic wherein like numbers refer to like compounds.

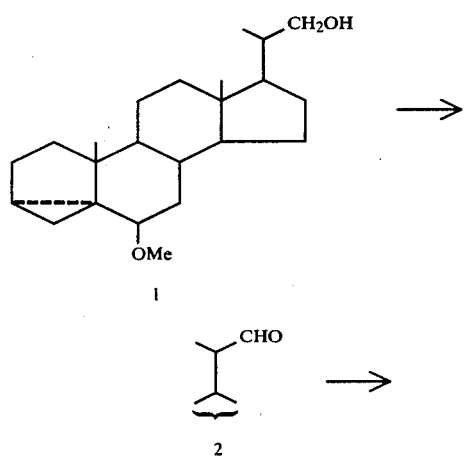

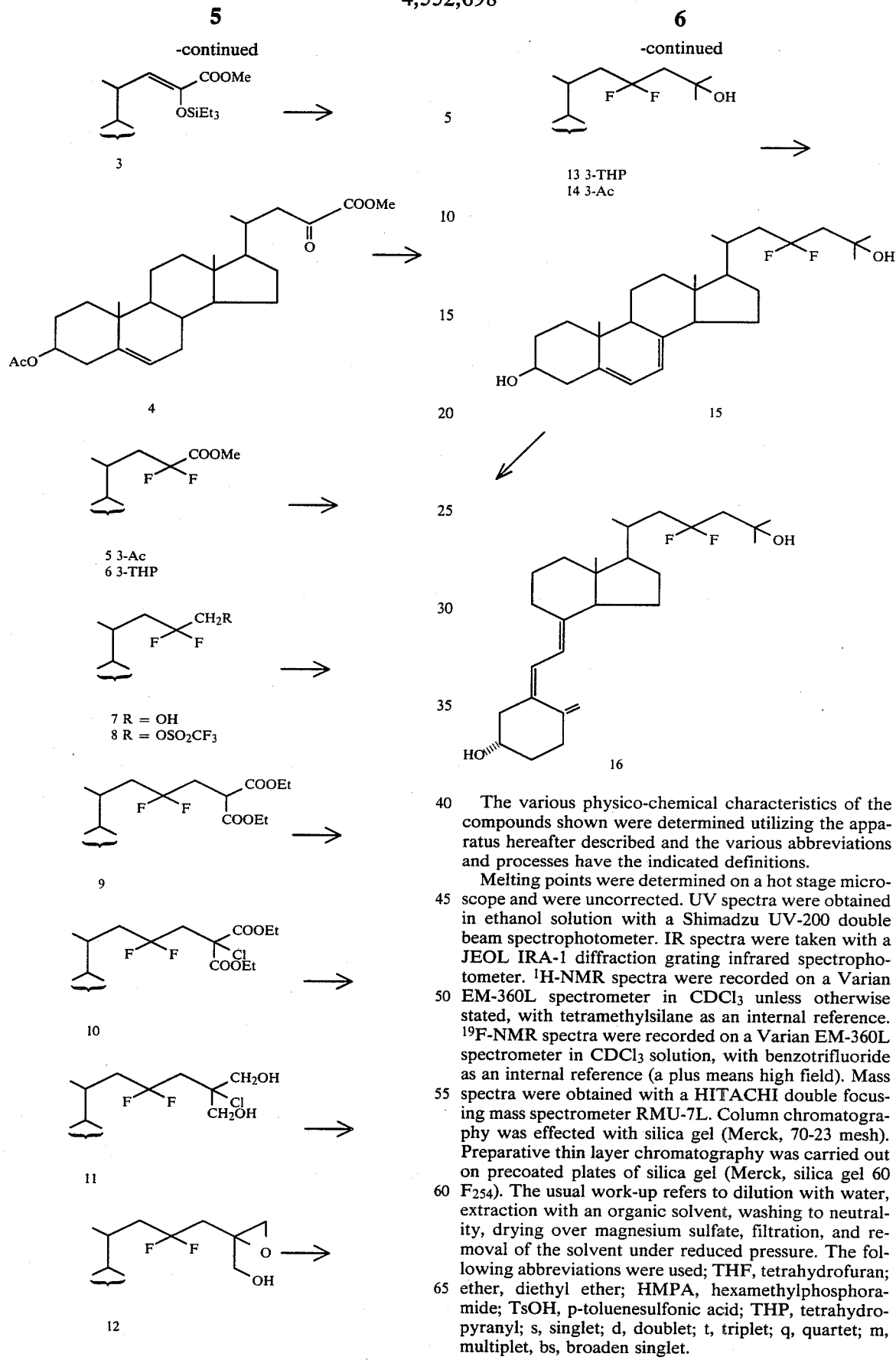

The various physico-chemical characteristics of the compounds shown were determined utilizing the apparatus hereafter described and the various abbreviations and processes have the indicated definitions.

Melting points were determined on a hot stage microscope and were uncorrected. UV spectra were obtained in ethanol solution with a Shimadzu UV-200 double beam spectrophotometer. IR spectra were taken with a JEOL IRA-1 diffraction grating infrared spectrophotometer. $^1$H-NMR spectra were recorded on a Varian EM-360L spectrometer in CDCl$_3$ unless otherwise stated, with tetramethylsilane as an internal reference. $^{19}$F-NMR spectra were recorded on a Varian EM-360L spectrometer in CDCl$_3$ solution, with benzotrifluoride as an internal reference (a plus means high field). Mass spectra were obtained with a HITACHI double focusing mass spectrometer RMU-7L. Column chromatography was effected with silica gel (Merck, 70-23 mesh). Preparative thin layer chromatography was carried out on precoated plates of silica gel (Merck, silica gel 60 F$_{254}$). The usual work-up refers to dilution with water, extraction with an organic solvent, washing to neutrality, drying over magnesium sulfate, filtration, and removal of the solvent under reduced pressure. The following abbreviations were used; THF, tetrahydrofuran; ether, diethyl ether; HMPA, hexamethylphosphoramide; TsOH, p-toluenesulfonic acid; THP, tetrahydropyranyl; s, singlet; d, doublet; t, triplet; q, quartet; m, multiplet, bs, broaden singlet.

SYNTHESIS

6β-Methoxy-3α,5-cyclo-23,24-dinor-5α-cholan-22-al (2)

6β-Methoxy-3,5-cyclo-23,24-dinor-5α-cholan-22-ol (1) (2.0 g, 15.8 mmol), which was prepared according to the literature method (see Helvetica Chimica Acta Vol. 57, Fasc. 3 (1974) nr. 84–85 pp 764–771) was added to suspension of pyridinium chlorate (3.8 g) and sodium acetate (1.4 g) in dichloro-methane (40 ml), and this mixture was stirred at room temperature for 2.5 hr. Then, to this solution ether (100 ml) was added and the resultant precipitates were filtered off and washed with ether (100 ml). The combined filtrate was succesively washed with 5% NaHCO$_3$ and brine, and dried over magnesium sulfate. After removal of the solvent in vacuo, the residue was applied to a column of silica gel (300 g). Elution with n-hexane-ether (10:1) provided the aldehyde (2) (1.44 g, 73%), amorphous. $^1$H-NMR δ: 0.76 (3H, s, 18-H$_3$), 1.30 (3H, d, J=6 Hz, 21-H$_3$), 1.17 (3H, s, 19-H$_3$), 2.76 (1H, m, 6-H), 3.33 (3H, s, —OCH$_3$), 9.51 (1H, d, J=3.5 Hz, —CHO). MS m/z: 344 (M$^+$), 329, 312.

6β-Methoxy-23-triethylsilyloxy-3α,5-cyclo-5α-cholan-22-en-24-oic Acid Methyl Ester (3)

To a solution of diisopropylamine (1.05 ml, 7.5 mmol) in THF (10 ml) n-butyllithium (6 mmol) was added at −78° C. under argon atmosphere and this solution was stirred for 5 min. To this solution methyl α-triethylsilyloxy-α-dimethylphosphonoacetate (1.56 g, 5 mmol) in THF (10 ml) was added and this mixture was stirred at room temperature for 15 min. Then, to the resulting solution the aldehyde (2) (491 mg, 1.43 mmol) in THF (10 ml) was added and this mixture was stirred at room temperature for 4 hr. The usual work-up (ether for extraction) gave a crude product, which was applied to a column of silica gel (150 g). Elution with n-hexane-ether (15:1) provided the unsaturated ester (3) (615 mg, 81%), colorless oil. $^1$H-NMR δ: 3.30 (3H, s, —OCH$_3$), 3.73 (3H, s, —CO$_2$CH$_3$), 5.26 (1H, d, J=10 Hz, 22-H). MS m/z: 530 (M$^+$), 501, 469.

3β-Acetoxy-23-oxochol-5-en-24-oic Acid Methyl Ester (4)

A solution of the unsaturated ester (3) (1.53 g, 2.9 mmol) in acetic acid (7 ml) was heated at 80°–90° C. for 6 hr. The usual work-up (ether for extraction) gave a crude product. This and a catalytic amount of TsOH in dioxane (10 ml) and water (10 ml) were heated at 85°–95° C. for 7 hr. The usual work-up (ether for extraction) gave a crude product, which was applied to a column of silica gel (300 g). Elution with n-hexane-ether (15:1) provided the α-keto ester (4) (768 mg, 76%), mp 146°–147° C. (n-hexane). IR $\gamma_{max}^{KBr}$ cm$^{-1}$: 1720, 1240. $^1$H-NMR δ: 0.73 (3H, s, 18-H$_3$), 0.93 (3H, d, J=6 Hz, 21-H$_3$), 1.03 (3H, s, 19-H$_3$), 2.03 (3H, s, acetyl), 3.88 (3H, s, —CO$_2$CH$_3$), 4.63 (1H, m, 3-H), 5.41 (1H, m, 6-H). MS m/z: 384 (M$^+$ —CH$_3$COOH), 369. Anal. Calcd. for C$_{27}$H$_{40}$O$_5$: C, 72.92; H, 9.08. Found: C, 72.63; H, 9.13.

3β-Acetoxy-23,23-difluorochol-5-en-24-oic Acid Methyl Ester (5)

A mixture of α-ketoester (4) (400 mg, 0.9 mmol) and diethylaminosulfurtrifluoride (1.5 ml, 9.5 mmol) in dichloromethane (15 ml) was stirred at room temperature for 16 hr. The usual work-up (ether for extraction) gave a crude product, which was applied to a column of silica gel (100 g). Elution with n-hexane-ether (10:1) provided the difluoroester (5) (312 mg, 74%), mp 132°–132.5° C. (n-hexane). IR $\gamma_{max}^{KBr}$ cm$^{-1}$: 1770, 1730, 1255. $^1$H-NMR δ: 0.70 (3H, s, 18-H$_3$),1.0. (3H, s, 19-H$_3$), 1.10 (3H, d, J=6 Hz, 21-H$_3$), 2.03 (3H, s, acetyl), 3.87 (3H, s, —CO$_2$CH$_3$), 4.60 (1H, m, 3-H), 5.38 (1H, m, 6-H). $^{19}$F-NMR: +40.3. MS m/z: 406 (M$^+$ —CH$_3$COOH). Anal. Calcd for CH$_{27}$H$_{40}$O$_4$F$_2$: C, 69.50; H, 8.64; F, 8.14. Found: C, 69.75; H, 8.75; F, 8.26.

23,23-Difluoro-3β-tetrahydropyranyloxychol-5-en-24-oic Acid Methyl Ester (6)

The difluoroester (5) (880 mg, 1.9 mmol) was treated with 2% KOH-MeOH (30 ml) at room temperature for 2 hr. The usual work-up (ether for extraction) gave a crude acid. This in ether (10 ml) was treated with ethereal solution of diazomethane until the gas evolution was ceased. This solution was concentrated under reduced pressure to leave the residue. This in dioxane (10 ml) was treated with 2,3-dihydropyran (516 μl) and TsOH (10 mg) at room temperature for 3 hr. The usual work-up (ether for extraction) gave a crude product, which was applied to a column of silica gel (200 g). Elution with n-hexane-ether (15:1) provided the THP-ester (6) (907 mg, 95%), amorphous. $^1$H-NMR δ: 0.70 (3H, s, 18-H$_3$), 1.03 (3H, s, 19-H$_3$), 1.10 (3H, d, J=6 Hz, 21-H$_3$), 3.53 (2H, m, THP), 3.86 (3H, s, —CO$_2$CH$_3$), 3.93 (1H, m, 3-H), 4.73 (1H, m, THP), 5.36 (1H, m, 6-H). $^{19}$F-NMR δ: +40.0. MS m/z: 424 (M$^+$-DHP), 406, 391.

23,23-Difluorochol-5-ene-3β,24-diol 3-THP Ether (7)

To a suspension of lithium aluminium hydride (63 mg, 1.65 mmol) in ether (10 ml) the difluoroester (6) (1.40 g, 2.76 mmol) in ether (10 ml) was added and the mixture was stirred at 0° C. for 10 min and then stirred at room temperature for 10 min. The usual work-up (ether for extraction) gave a crude product, which was applied to a column of silica gel (100 g). Elution with n-hexane-ether (5:1) gave the alcohol (7) (1.13 g, 86%), viscous oil. $^1$H-NMR δ: 0.73 (3H, s, 18-H$_3$), 1.03 (3H, s, 19-H$_3$), 1.13 (3H, d, J=6 Hz, 21-H$_3$), 3.33–4.10 (5H, m, 24-H$_2$, 3-H, and THP), 4.76 (1H, m, THP), 5.38 (1H, m, 6-H). $^{19}$F-NMR δ: +43.3. MS m/z: 396 (M$^+$-DHP), 378.

23,23-Difluoro-24-trifluoromethanesulfonyloxychol-5-en-3β-ol 3-THP Ether (8)

The mixture of pyridine (124 μl) and trifluoromethanesulfonic anhydride (206 μl) in dichloromethane (5 ml) was stirred at −20° C. under argon atmosphere for 5 min. To this solution the alcohol (7) (400 mg, 1.02 mmol) in dichloromethane (10 ml) was added and the mixture was stirred at room temperature for 40 min. The usual work-up (dichloromethane for extraction) gave the triflate (8) (612 mg), which was used in the next step without further purification. $^1$H-NMR δ: 0.73 (3H, s, 18-H$_3$), 1.00 (3H, s, 19-H$_3$), 1.15 (3H, d, J=6 Hz, 21-H$_3$), 3.56 (2H, m, THP), 3.85 (1H, m, 3-H), 4.50 (2H, t, J=12 Hz, 24-H$_2$), 4.70 (1H, m, THP), 5.37 (1H, m, 6-H). $^{19}$F-NMR δ: +12.2 (3F), +41.3 (2F).

23,23-Difluoro-3β-tetrahydropyranyloxycholest-5-ene-26,27-dioic Acid Diethyl Ester (9)

A mixture potassium tert-butoxide (1.1 g, 9.6 mmol) and diethyl malonate (3.8 g, 24 mmol) in THF (25 ml) and HMPA (8 ml) was stirred at room temperature under argon atmosphere for 1 hr. To this solution the triflate (8) (1.47 g, 2.4 mmol) in THF (20 ml) was added and the mixture was stirred at room temperature for 26 hr. The usual work-up (ether for extraction) gave a crude product, which was applied to a column of silica gel (100 g). Elution with n-hexane-ether (5:1) provided the diester (9) (1.20 g, 81%), mp 79°–80° C. (ethanol). IR $\gamma_{max}^{KBr}$ cm$^{-1}$: 1750, 1740. $^1$H-NMR δ: 0.73 (3H, s, 18-H$_3$), 1.00 (3H, s, 19-H$_3$), 1.10 (3H, d, J=6 Hz, 21-H$_3$), 1.27 (6H, t, J=7 Hz, —CO$_2$CH$_2$CH$_3$), 3.46 (2H, m, THP), 3.62 (1H, t, J=6 Hz, 25-H), 3.80 (1H, m, 3-H), 4.14 (4H, q, J=JHz, —COCH$_2$CH$_3$), 4.64 (1H, m, THP), 5.30 (1H, m, 6-H). MS m/z: 538 (M$^+$-DHP), 520, 505. Anal. Calcd for C$_{36}$H$_{56}$O$_6$F$_2$: C, 69.40; H, 9.06; F, 6.10. Found: C, 69.19; H, 9.11; F, 5.85.

25-Chloro-23,23-difluoro-3β-tetrahydropyranyloxy-cholest-5-ene-26,27-dioic Acid Diethyl Ester (10)

The diester (9) (700 mg, 1.125 mmol) was treated with sodium hydride (39 mg, 1.625 mmol) in dimethoxyethane (20 ml) at room temperature under argon atmosphere for 1 hr. Then, to this solution N-chlorosuccinimide (180 mg, 1.35 mmol) was added and the mixture was stirred at room temperature for 1 hr. The usual work-up (ether for extraction) gave a crude product, which was applied to a column of silica gel (20 g). Elution with n-hexane-ether (10:1) provided the chlorodiester (10) (730 mg, 99%), glass. $^1$H-NMR: 0.72 (3H, s, 18-H$_3$), 1.02 (3H, s, 19-H$_3$), 1.10 (3H, d, J=6 Hz, 21-H$_3$), 1.30 (6H, t, J=7.5 Hz, —CO$_2$CH$_2$CH$_3$), 2.95 (2H, t, J=15 Hz, 24-H$_2$), 3.52 (2H, m, THP), 3.88 (1H, m, 3-H), 4.32 (4H, q, J=7.5 Hz, —CO$_2$CO$_2$CH$_3$), 4.72 (1H, m, THP), 5.38 (1H, m, 6-H). MS m/z: 554, 520.

25-Chloro-23,23-difluorocholest-5-ene-3β,26,27-triol 3-THP Ether (11)

To a solution of the chlorodiester (10) (730 mg, 1.1 mmol) in ether (15 ml) lithium aluminium hydride (48 mg) was added and the mixture was stirred at 0° C. for 1 hr. and then stirred at room temperature for 2 hr. The usual work-up (ether for extraction) gave a crude product, which was applied to a column of silica gel (50 g). Elution with dichloromethane provided the chlorodiol (11) (250 mg, 39%) mp 152°–153° C. (n-hexane-ether). $^1$H-NMR δ(CDCl$_3$-acetone d$_6$-DMSO d$_6$): 0.77 (3H, s, 18-H$_3$), 1.00 (3H, s, 19-H$_3$), 1.10 (3H, d, J=6 Hz, 21-H$_3$), 3.50-4.50 (7H, m, 3-H, 26-H$_2$, 27-H$_2$, and THP), 4.77 (3H, m, 26-OH, 27-OH, and THP), 5.38 (1H, m, 6-H); δ(CDCl$_3$-acetone d$_6$-DMSOd$_6$-D$_2$O): 3.60 (2H, m, THP), 3.77 (4H, s, 26-H$_2$ and 27-H$_2$), 4.77 (1H, m, THP). MS m/z: 434, 416, 404. Anal. Calcd for C$_{32}$H$_{51}$O$_4$ClF$_2$: C, 67.05; H, 8.97; Cl, 6.19; F, 6.63. Found: C, 67.08; H, 8.89; Cl, 5.99; F, 6.53.

25ε)-25,26-Epoxy-23,23-difluorocholest-5-ene-3β,27-diol 3-THP Ether (12)

The chlorodiol (11) (183 mg, 0.32 mmol) was treated with sodium hydride (18 mg, 0.75 mmol) in dimethoxyethane (18 ml) at room temperature for 6 days. The usual work-up (ether for extraction) gave a crude product, which was applied to a column of silica gel (100 g). Elution with dichloromethane provided the epoxyalcohol (12) (56 mg, 32%), glass. $^1$H-NMr δ: 2.92 (2H, m, 26-H$_2$), 3.67-4.16 (3H, m, 3-H and 27-H$_2$). MS m/z: 434 (M$^+$-THP OH), 416, 404, and the recovery of chlorodiol 11 (92 mg, 50%).

23,23-Difluorocholest-5-ene-3β,25-diol 3-THP Ether (13)

The epoxyalcohol (12) (55 mg, 0.103 mmol) was treated with methanesulfonyl chloride (20 μl) and triethylamine (30 μl) in dichloromethane (10 ml) at room temperature for 13 hr. The usual work-up (ether for extraction) gave the crude mesylate (69 mg). This mesylate was treated with lithium aluminum hydride (5 mg) in ether (10 ml) at 0° C. for 1.5 hr. The usual work-up (ether for extraction) gave a crude product, which was applied to a column of silica gel (20 g). Elution with n-hexane-ether (5:2) provided the 25-ol (13) (43.3 mg, 80%), mp 148°–149° C. (n-hexane-cyclohexane). $^1$H-NMR δ: 0.72 (3H, s, 18-H$_3$), 1.01 (3H; s,19-H$_3$), 1.10(3H, d, J=6 Hz, 21-H), 1.35 (6H, s, 26-H$_3$ and 27-H$_3$), 3.53 (2H, m, THP), 3.87 (1H, m, 3-H), 4.71 (1H, m, THP), 5.37 (1H, m, 6-H). MS m/z: 420 (M$^+$-TEPOH), 405. High resolution MS Calcd for C$_{27}$H$_{42}$F$_2$O (M$^+$-THPOH): 420, 3214. Found: 420, 3208.

23,23-Difluorocholest-5-ene-3β,25-diol 3-Acetate (14)

The THP-ether (13) (26 mg, 0.0498 mmol) in methanol (4 ml) and THP (9) (4 ml) was treated with a catalytic amount of TsOH at room temperature for 1 hr. The usual work-up (ethyl acetate for extraction) gave the crude diol (21.4 mg). This diol was treated with acetic anhydride (1 ml) and pyridine (1 ml) at room temperature for 14 hr. The usual work-up (ethyl acetate for ertraction) gave a crude product, which was applied to a column of silica gel (5 g). Elution with benzene-ethyl acetate (10:1) provided the acetate (14) (23.0 mg, 96%); mp 168°–170° C. (methanol). $^1$H-NMR δ: 0.82 (3H, s, 18-H$_3$), 1.02 (3H, s, 19-H$_3$), 1.07 (3H, d, J=6 Hz, 21-H$_3$), 1.35 (6H, s, 26-H$_3$ and 27-H$_3$), 2.03 (3H, s, acetyl), 4.55 (1H, m, 3-H), 5.36 (1H, m, 6-H). High resolution MS Calcd for C$_{27}$H$_{42}$F$_2$O (M$^+$ —CH$_3$COOH): 420, 3202. Found: 420, 3206.

23,23-Difluorocholesta-5,7-diene-3,25-diol (15)

To a solution of the acetate (14) (19 mg, 0.0396 mmol) in carbontetrachloride (2 ml) N-bromosuccinimide (10 mg, 0.0571 mmol) was added and this mixture was refluxed under argon atmosphere for 20 min. After cooling to 0° C., the resulting precipitate was filtered off. The filtrate was concentrated below 40° C. to leave the residue. This residue in xylene (2 ml) was added dropwise to a refluxing solution of S-collidine (0.5) and xylene (1.5 ml) and refluxing was continued for 20 min. The usual work-up (ethyl acetate for extraction) gave the crude diene. This diene in acetone (10 ml) was treated with a catalytic amount of TsOH at room temperature under argon atmosphere in the dark for 14 hr. The usual work-up (ethyl acetate for extraction) gave the crude 5,7-diene acetate. This acetate in THF (5 ml) was treated with 5% KOH-MeOH (1.0 ml) at room temperature under argon atmosphere in the dark for 30 min. The usual work-up (ethyl acetate for extraction) gave a crude product, which was submitted to preparative TLC (benzene-ethyl acetate 2:1, developed twice). The band of Rf value 0.47 was scraped off and eluted with ethyl acetate. Removal of the solvent provided the 5,7-diene (15) (3.75 mg, 21.7%). UV λ$_{max}$ mm: 294, 282, 272.

23,23-Difluoro-25-hydroxyvitamin D$_3$ (16)

A solution of the 5,7-diene (15) (3.75 mg, 8.60 μmol) in benzene (90 ml) and ethanol (40 ml) was irradiated with a medium pressure mercury lamp through a Vycor filter with ice cooling under argon atmosphere for 2.5 min. Removal of the solvent under reduced pressure gave a crude product, which was submitted to preparative TLC (benzene-ethyl acetate 2:1, developed twice). The band of Rf value 0.59 was scraped off and eluted with ethyl acetate. Removal of the solvent provided the vitamin D$_3$ derivative (16) (0.96 mg, 25.6%). This was further purified by high performance liquid chromatography on a Zorbax SIL normal phase column (4.6 mmΦ×15 cm) at a flow rate of 2 ml/min with hexane-dichloromethane (1:2) as an eluent. The retention time of (16) was 7.4 min. UV λ$_{max}$ nm: 265, λ$_{min}$ nm: 228. $^1$H-NMR δ: 0.58 (3H, s, 18-H$_3$), 1.07 (3H, d, J=6.1 Hz, 21-H$_3$) 1.34 (6H, s, 26-H$_3$ and 27-H$_3$), 3.95 (1H, m; 3-H), 4.81 (1H, bs, 19-H), 5.04 (1H, bs, 19-H), 6.03 (1H, d, J=10.7 Hz, 7-H), 6.23 (1H, d, J=10.7 Hz, 6-H). MS m/z: 436 (M+), 418, 403, 398, 380, 378, 300, 271, 265, 145, 118: High resolution MS calcd for $C_{27}H_{42}F_2O_2$: 436, 3150. Found: 436, 3155.

It will be apparent that in the foregoing other reactants may be utilized which will provide equivalent substituents at various places in the compounds depicted in the abreviated

BIOLOGICAL ACTIVITY

The biological activity of the new analog is evidenced by appropriate in vivo assays in the rat.

Male weanling rats (Holtzman, Company, Madison, Wis.) were fed a low calcium vitamin D-deficient diet (0.02% calcium, 0.3% phosphorous—J. Nut. 100, 1045–1052 (1970)) for two weeks. They were divided into three groups of 6–7 rats each. Rats in the control group were given 0.05 ml of 95% ethanol by intrajugular injection. Rats in the other two groups were each administered, in the same manner, a dose, respectively, of 100 pmoles of 1,25-dihydroxyvitamin $D_3$(1,25-$(OH)_2D_3$) in 0.05 ml of ethanol or 23,23-difluoro-1α,25-dihydroxyvitamin $D_3$ (23,23-$F_2$-1,25-$(OH_2)D_3$ in 0.05 ml ethanol. 96 hours after dosing the effect of the compounds on intestinal calcium transpsort was determined by the method of Martin and DeLuca (Am. J. Physiol. 216, 1351–1359, 1969). Results are shown in the Table below.

TABLE 1

| Compound Given | Intestinal Calcium Transport (Ca serosol/Ca mucosal) (Avg. ± SEM) |
|---|---|
| None (vehicle only) | 2.6 ± 0.1[a] |
| 1,25-$(OH)_2D_3$ | 4.6 ± 0.4[b] |
| 23,23-$F_2$—1,25-$(OH)_2D_3$ | 4.5 ± 0.3[c] |

Significance of difference: [b] & [c] from [a] p 0.001

The foregoing data indicate that 23,25-$F_2$1,25-$(OH)_2D_3$ is as active in promoting intestinal calcium transport as the circulating hormonal form of vitamin $D_3$, 1,25-$(OH_2)D_3$, strongly suggesting its use as a substitute for the hormonal form of the vitamin where pharmacologically increased intestinal calcium transport is indicated.

The 23,23-difluoro-1α,25-dihydroxycholecalciferol compound of this invention may be readily administered as sterile parenteral solutions by injection or intravenously or by alimentary canal in the form of oral dosages, or by suppository. Doses of from about 0.1 μg to about 10 μg per day are effective in obtaining the physiological calcium balance responses described and which are characteristic of vitamin D-like activity, with maintenance doses of about 0.25 μg being suitable.

Dosage form of the compounds can be prepared by combining them with a non-toxic pharmaceutically acceptable carrier as is well known in the art. Such carriers may be either solid or liquid such as, for example, corn starch, lactose, sucrose, peanut oil, olive oil, sesame oil and water. If a solid carrier is used the dosage forms of the compounds of the invention may be tablets, capsules, powders, troches or lozenges. If a liquid carrier is used, soft gelatin capsules, or syrup or liquid suspensions, emulsions or solutions may be the dosage form. The dosage forms may also contain adjuvants, such as preserving, stabilizing, wetting or emulsifying agents, solution promoters, etc. They may also contain other therapeutically valuable substances.

It should be understood that although dosage ranges are given the particular dose to be administered to a host will depend upon the specific disease state being treated, the end results being sought in a particular case, as well as other factors known to those skilled in the art in the therapeutic use of such medicinal agents.

We claim:

1. Compounds having the formula

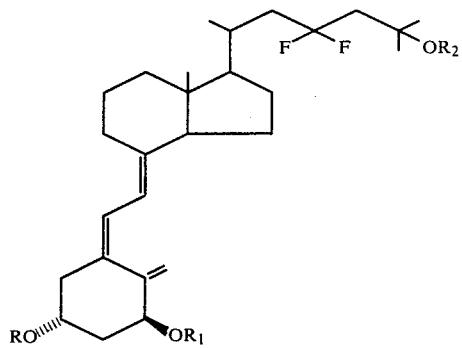

wherein each of R, $R_1$ and $R_2$ is selected from the group consisting of hydrogen, an acyl group having from one to about four carbon atoms and benzoyl with the proviso that R, $R_1$ and $R_2$ cannot all be hydrogen.

2. The compound according to claim 1 wherein R, $R_1$ and $R_2$ are acetyl.

3. The compound according to claim 1 wherein R, $R_1$ and $R_2$ are benzoyl.

4. The compounds of claim 1 in crystalline form.